United States Patent [19]

Hase et al.

[11] 4,128,634
[45] Dec. 5, 1978

[54] COSMETIC EMULSIONS CONTAINING COPOLYMERS OF ALKYL(METH)ACRYLATES AND MONO-(N-HYDROXYALKYL) OR BIS-(N-HYDROXYALKYL) (METH)ACRYLAMIDES

[75] Inventors: Brigitte Hase, Erkrath; Joachim Galinke, Langenfeld; Bernd Wegemund, Haan, all of Fed. Rep. of Germany

[73] Assignee: Henkel Kommanditgesellschaft auf Aktien, Düsseldorf-Holthausen, Fed. Rep. of Germany

[21] Appl. No.: 773,606

[22] Filed: Mar. 2, 1977

[30] Foreign Application Priority Data

Mar. 4, 1976 [DE] Fed. Rep. of Germany ....... 2608834

[51] Int. Cl.$^2$ ............................................. A61K 31/78
[52] U.S. Cl. ..................................................... 424/81
[58] Field of Search .......... 424/81; 260/23 R, 28.5 R, 260/29.6 R

[56] References Cited

U.S. PATENT DOCUMENTS

| 3,574,822 | 4/1971 | Shepherd et al. | 424/81 |
| 3,577,517 | 5/1971 | Kubot et al. | 424/81 |
| 3,577,518 | 5/1971 | Shepherd et al. | 424/81 |
| 3,728,314 | 4/1973 | Blank | 424/81 |
| 3,755,560 | 8/1973 | Dickert et al. | 424/81 |
| 3,914,405 | 10/1975 | Shepherd et al. | 424/81 |
| 3,927,199 | 12/1975 | Micchelli et al. | 424/81 |
| 3,927,203 | 12/1975 | Seymour et al. | 424/81 |

FOREIGN PATENT DOCUMENTS

2116787 10/1971 Fed. Rep. of Germany.

*Primary Examiner*—Donald B. Moyer
*Attorney, Agent, or Firm*—Hammond & Littell

[57] ABSTRACT

Water-in-oil emulsions containing from 2% to 20% by weight of polymeric emulsifiers comprising statistical copolymers composed of units of the general formulae

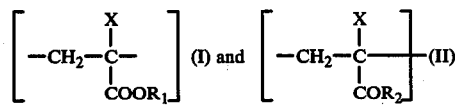

in the molar ratio of (I) to (II) of 2:1 to 20:1, wherein X is hydrogen or methyl, $R_1$ is alkyl having 6 to 24 carbon atoms, and $R_2$ is $-NH-CH_2OH$, $-NH-CH_2CH_2OH$, or $-N(CH_2CH_2OH)_2$; 20 to 75% by weight of water; and the remainder to 100% by weight of conventional oily substances used in cosmetic emulsions.

10 Claims, No Drawings

COSMETIC EMULSIONS CONTAINING COPOLYMERS OF ALKYL(METH)ACRYLATES AND MONO-(N-HYDROXYALKYL) OR BIS-(N-HYDROXYALKYL) (METH)ACRYLAMIDES

FIELD OF THE INVENTION

The invention relates to cosmetic emulsions of the water-in-oil type having a content of copolymers of alkyl(meth)acrylates and mono-(N-hydroxyalkyl) or bis-(N-hydroxyalkyl) (meth)acrylamides as emulsifiers. The invention includes the emulsions themselves and methods for the preparation thereof.

RELATED ART

In contrast to the production of oil-in-water emulsions, only a limited number of emulsifying agents are available for producing cosmetic emulsions of the water-in-oil type and, moreover, the best of these emulsifying agents are becoming increasingly scarce. Even nowadays, wool fat and its derivatives are still some of the most important bases for emulsifying agents for producing creams of the water-in-oil type. However, despite their uncontested advantages, both wool fat and its derivatives, such as lanolin, have certain disadvantages. Thus conventional water-in-oil emulsifying agents based on wool fat and its derivatives impart a strong characteristic odor to the creams prepared with these substances. This, in turn, requires strong perfuming which frequently cannot be tolerated by persons having sensitive skin. However, this influencing of the quality of the cream by a strong characteristic odor is not only peculiar to wool fat and its derivatives, but also extends to lanolin-free water-in-oil emulsifying agents based on animal sterols, particularly such emulsifying agents based on cholesterol. Furthermore, low-molecular weight emulsifying agents, together with the effective substances of the cream, can be absorbed by the skin, which is not desirable in all cases.

In addition to the said emulsifying agents based on wool fat, wax alcohols and sterols, the most widely known water-in-oil emulsifiers for cosmetic purposes include the oleic acid esters for various polyols, such as glycerin, pentaerythritol, trimethylolpropane and sorbitol. However, due to the unsaturation in their acid component the oleic acid esters have various disadvantages with respect to their technical use, so that there is a genuine need for new and suitable water-in-oil emulsifying agents.

OBJECTS OF THE INVENTION

One object of the present invention is the development of a cosmetic emulsion or cream of the water-in-oil type which can be prepared easily and safely from inexpensive materials without need for costly emulsifying equipment.

Another object of the invention is the development of a cosmetic emulsion of the above type which is substantially odorless and which, therefore, can find general acceptance when containing only a small and harmless amount of perfume.

A particular object of the invention is the production of a cosmetic emulsion of the above type comprising (1) from 2% to 20% by weight of a polymeric emulsifier capable of forming water-in-oil emulsions composed of units of the general formulae

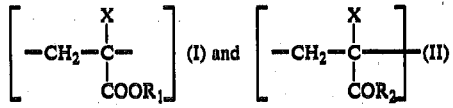

in the molar ratio of (I) to (II) of 2:1 to 20:1, wherein X is hydrogen or methyl, $R_1$ is alkyl having 6 to 24 carbon atoms and $R_2$ is $-NH-CH_2OH$, $-NH-CH_2CH_2OH$, or $-N(CH_2CH_2OH)_2$; (2) from 20 to 75% by weight of water; and (3) the remainder to 100% by weight of conventional oily substances used in cosmetic emulsions.

These and other objects of the present invention will become more apparent as the description thereof proceeds.

DESCRIPTION OF THE INVENTION

It has now been disovered that the objectionable features of the prior art emulsifiers have been overcome and the above objects have been achieved by the discovery of cosmetic emulsions of the water-in-oil type containing (1) from 2% to 20% by weight, relative to the total weight of the emulsion, of statistical copolymers, which are composed, in the molar ratio of (I) to (II) of 2:1 to 20:1, more preferably 3:1 to 12:1, of units of the general formulae

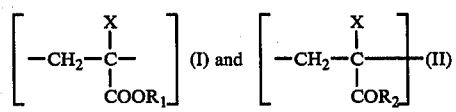

wherein X is hydrogen or a methyl radical, $R_1$ is an alkyl radical of 6 to 24 carbon atoms, and $R_2$ is a radical selected from the group consisting of $-NH-CH_2OH$, $-NH-CH_2CH_2OH$, and $-N(CH_2CH_2OH)_2$, (2) from 20% to 75% by weight of water, relative to the total weight of the emulsion, and (3) the remainder to 100% by weight of conventional oil substances used in cosmetic emulsions, such as vegetable and animal fats, waxes, fatty alcohols, hydrocarbons, as well as other auxiliary substances normally used in cosmetic emulsions.

The preparation of the copolymers of alkyl(meth)acrylates and mono-(N-hydroxyalkyl) or bis-(N-hydroxyalkyl) (meth)acrylamides used as emulsifiers in the cosmetic emulsions of the invention can be effected in known manner in one step under the usual conditions of radical polymerization. The polymerization can be carried out with nonpolar solvents, such as benzene or toluene, or in polar solvents, such as methanol, methyl ethyl ketone or tetrahydrofuran, by means of peroxides, such as dibenzoyl peroxide or lauroyl peroxide, and azo compounds, such as azobisisobutyronitrile as a catalyst.

The technical production is preferably effected in the form of a solution polymerization, in those solvents which dissolve only the monomers, but not the polymer (precipitation polymerization) particularly since this results in satisfactorily precipitable polymers which are practically free of monomers (J. Scheiber, Chemie und Technologie der Künstlichen Harze, Vol. I, pages 362 ff, 1961.

The monomeric starting compounds from which the polymer units (II) of the copolymers of the invention are derived are mono- or bis-(N-hydroxyalkyl) (meth)

acrylamides which are in part commercially available products, such as N-hydroxymethyl acrylamide, or products which are known in the literature, such as N-hydroxymethyl methacrylamide, (C.A. 66, pg. 66, 705 c), N-2-hydroxyethyl acrylamide (C.A. 66, p. 29, 497 r), N-2hydroxyethyl methacrylamide (C.A. 64, p. 1970, g), bis-(n-2-hydroxyethyl) acrylamide, (C.A. 66, p. 29, 497 r) and bis- N-2-hydroxyethyl)methacrylamide (C.A. 56, p. 1616,i). They are prepared by methods known in the art.

Examples of such monomeric starting compounds are N-hydroxymethyl acrylamide, N-hydroxymethyl methacrylamide, N-2-hydroxyethyl acrylamide, and bis-(N-2-hydroxyethyl) methacrylamide. N-hydroxymethyl acrylamide has been found to be a very useful monomer.

The monomeric starting compounds from which the polymer units (I) of the copolymers of the invention are derived have the formula

wherein X is hydrogen or methyl, and $R_1$ is an alkyl radical having 6 to 24, more preferably 8 to 14, carbon atoms.

Among the monomeric starting compounds of the formula (III) above may be mentioned hexyl acrylate, octyl acrylate, 2-ethylhexyl acrylate, nonyl acrylate, decyl acrylate, lauryl acrylate, myristyl acrylate, cetyl acrylate stearyl acrylate, behenyl acrylate, hexyl methacrylate, octyl methacrylate, nonyl methacrylate, decyl methacrylate, lauryl methacrylate, myristyl methacrylate, cetyl methacrylate, stearyl methacrylate and behenyl methacrylate.

Among the preferred monomers of the formula (III) are the acrylic and methacrylic acid esters of the fatty alcohols having 8 to 14 carbon atoms in the alkyl radical such as octyl acrylate, nonyl acrylate, decyl acrylate, lauryl acrylate, myristyl acrylate, octyl methacrylate, nonyl methacrylate, decyl methacrylate, lauryl methacrylate, and myristyl methacrylate.

In the copolymers of the invention, the molar ratio of the mono- or bis-(N-hydroxyalkyl) (meth) acrylamide monomer: alkyl (meth) acrylate monomer are from 1:2 to 1:20, preferably from 1:3 to 1:12.

The copolymers of the invention have average molecular weights between 2,000 and 100,000. Those having average molecular weights between 3,000 and 20,000 are particularly suitable in view of their easy processability and the quality of the emulsions obtained. These molecular weights can be adjusted in a known manner by the amount of catalyst, the nature and amount of the solvent, and by the addition of polymerization regulators.

The emulsions in accordance with the invention are produced in a simple and known manner by dissolving the copolymers, acting as the emulsifying agents, in the oil phase at a temperature of approximately 60° to 70° C. Subsequently, the desired quantity of water, heated to approximately 60° C. to 65° C. is added, and the emulsion obtained is stirred while cooling.

Cosmetically effective amounts of further constituents of the cosmetic emulsions being manufactured, such as skin moisture regulators, vegetable extracts of effective substances, vitamins, hormones, pigments, salts, perfume oils, UV filtering substances, dyestuffs, etc., are advantageously dissolved or distributed in the phase which absorbs these substances to best advantage. The quantity of emulsifying agent required is 2% to 20% by weight, preferably 5% to 10% by weight, relative to the total cosmetic emulsion. The amount of water to be incorporated can be 20% to 75% by weight, preferably 45% to 65% by weight, relative to the total cosmetic emulsion.

Products conventionally used, such as animal and vegetable oils and fats, synthetic esters or fatty acids with aliphatic alcohols, higher fatty alcohols, waxes, so-called mineral fats and oils, such as paraffin oil, "Vaseline" ®, ceresine, silicone oils and silicone fats are suitable as the oil phase of the cosmetic emulsions in accordance with the invention.

The invention thus also includes a composition which when agitated with water forms a cosmetic emulsion of the water-in-oil type, comprising (1) from 2% to 20% by weight, relative to the total weight of said composition, of a polymeric emulsifier which is a copolymer composed, in the molar ratio of (I) to (II) of 2:1 to 20:1, of units of the general formulae

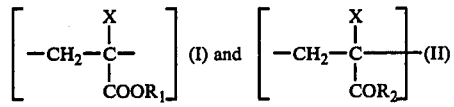

wherein X is hydrogen or a methyl radical, $R_1$ is an alkyl radical of 6 to 24 carbon atoms, and $R_2$ is a radical selected from the group consisting of $-NH-CH_2OH$, $-NH-CH_2CH_2OH$, and $-N(CH_2CH_2OH)_2$, and (2) the remainder to 100% by weight of the composition of conventional oily substances used in cosmetic emulsions. Such conventional oily substances include animal and vegetable oils and fats, synthetic esters of fatty acids with aliphatic alcohols, higher fatty alcohols, waxes, so-called mineral fats and oils, such as paraffin oil, "Vaseline" ®, ceresin, silicone oils and silicone fats. In addition the cosmetic emulsions or creams can contain, if desired, other auxiliary substances normally used in cosmetic emulsions. Examples of such auxiliary substances are skin moisture regulators, vegetable extracts of effective substances, vitamins, hormones, pigments, salts, perfume oils, UV filtering substances, dyestuffs, etc.

German Offenlegungsschrift (DOS) No. 2,116,787 has already described the use of water-in-oil emulsifying agents in the form of sequence polymers which at the same time have at least one lipophilic sequence and one hydrophilic sequence. Each sequence should have the properties of the corresponding homopolymer. These sequence polymers are obtained by anionic polymerization, which places high demands on the purity of the substances used, and requires working at low temperatures under protective gas and increased safety precautions when handling spontaneously combustible catalysts. In contrast to this, the emulsifying agents required for producing the emulsions in accordance with the present invention can be manufactured in a simple manner.

According to German Offenlegungsschrift (DOS) No. 1,745,216, copolymers of a monomer with a lipophilic chain and a monomer with a carboxylic acid anhydride function are suggested as emulsifiers for water-in-oil emulsions. But these products are sensitive to hydrolysis, and, to avoid this disadvantage, a further processing step in addition to the polymerization, is required in order to convert them into a more stable form.

In general, the emulsions in accordance with the present invention can also be used by persons having a sensitive skin. Since they do not have any appreciable characteristic odor, they do not require heavy perfuming, which in turn, has an advantageous effect upon the compatibility and also reduces costs.

Furthermore, the emulsions according to the invention are characterized by low sensitivity to acid, thus rendering it possible to incorporate acidic raw materials therein, such as organic acids. Another very favorable property of the emulsions according to the invention is their high temperature stability, which enables them to withstand a thermal stress of 50° C. for 6 weeks without any detrimental effects.

In the specification and claims, the term "(meth)acrylate(s)" is used to designate ester(s) of acrylic acid and ester(s) of methacrylic acid. Similarly, the term "(meth)acrylamide(s)" is used to designate amide(s) of acrylic acid and amide(s) of methacrylic acid.

The following examples further illustrate the invention, but without limiting the invention to these examples.

EXAMPLES

The following example illustrates the preparation of a copolymer for use in the cosmetic emulsions of the present invention.

EXAMPLE 1

N-Hydroxymethyl acrylamide/dodecyl acrylate-copolymer (1:6 molar ratio)

10.1 gm (0.1 mole) of N-hydroxymethyl acrylamide and 144 gm (0.6 mole) of dodecyl acrylate were dissolved in 360 gm of methyl ethyl ketone. To the solution obtained were added 3.1 gm of dibenzoyl peroxide as a catalyst. The reaction mixture was maintained for 5 hours under stirring at a temperature of 80° C. After the reaction was completed, the solvent was distilled off and the reaction product washed several times with methanol. 147 gm (95% of theory) of N-hydroxymethyl acrylamide/dodecyl acrylate copolymer (1:6 molar ratio) were obtained.

The other copolymers, used in the examples given below, were obtained in an analogous manner to the above method.

EXAMPLE 2

Cosmetic emulsions based on Vaseline ®

A mixture of 10 gm of N-hydroxymethyl acrylamide/dodecyl acrylate copolymer (1:6 molar ratio), and 40 gm of Vaseline ® was melted together by heating to 65° C. To the melt was added 50 gm of water, which had been heated to 65° C., and the mass was allowed to cool under constant stirring. The emulsion can be easily produced by manual stirring. The cream is stable for several months and showed no change even after 6 weeks at 50° C. By adding various conventional cosmetic agents and perfume oils, this basic cream can be used to produce various skin creams.

The following copolymers can also be used in the foregoing example instead of N-hydroxymethyl acrylamide/dodecyl acrylate copolymer (1:6 molar ratio) with equally good results.

| Copolymer | Molar Ratio |
| --- | --- |
| N-hydroxymethyl acrylamide/decyl acrylate | (1:3) |
| N-hydroxymethyl acrylamide/behenyl acrylate | (1:2) |
| N-hydroxymethyl acrylamide/octyl acrylate | (1:12) |
| N-hydroxymethyl acrylamide/hexyl acrylate | (1:15) |
| N-hydroxymethyl acrylamide/cetyl acrylate | (1:8) |
| N-hydroxymethyl methacrylamide/decyl acrylate | (1:10) |
| N-hydroxymethyl methacrylamide/octyl methacrylate | (1:8) |
| N-2-hydroxyethyl acrylamide/dodecyl methacrylate | (1:6) |
| N-2-hydroxyethyl acrylamide/myristyl acrylate | (1:4) |
| N-2-hydroxyethyl methacrylamide/stearyl acrylate | (1:2) |
| N-2-hydroxyethyl methacrylamide/decyl methacrylate | (1:8) |
| bis-(N-2-hydroxyethyl)acrylamide/hexyl acrylate | (1:20) |
| bis-(N-2-hydroxyethyl)acrylamide/octyl acrylate | (1:12) |
| bis-(N-2-hydroxyethyl)acrylamide/dodecyl methacrylate | (1:8) |
| bis-(N-2-hydroxyethyl)methacrylamide/myristyl acrylate | (1:6) |
| bis-(N-2-hydroxyethyl)methacrylamide/nonyl methacrylate | (1:10) |

EXAMPLE 3

Cosmetic emulsion based on peanut oil/decyl oleate mixture

A mixture of 4 gm of N-hydroxymethyl acrylamide/dodecyl acrylate copolymer (1:6 molar ratio), 40 gm of a hardened peanut oil/decyl oleate mixture (90:10 by weight), 3 gm of beeswax, and 3 gm of glyceryl monooleate was melted together by heating to 70° C. To the melt were added under constant stirring 50 gm of water, which had been heated to 65° C., and the paste was allowed to cool under constant stirring. A cream was obtained which was very similar in its stability properties to the cream obtained in Example 2. By incorporating additional cosmetically effective amounts of conventional cosmetically effective substances, such as moisture regulators, vegetable extracts, and perfume oils, various skin creams can be prepared from this basic cream.

The following copolymers can be used instead of N-hydroxymethyl acrylamide/dodecyl acrylate copolymer (1:6 molar ratio) with equally good results.

| Copolymer | Molar Ratio |
| --- | --- |
| N-hydroxymethyl acrylamide/cetyl acrylate | (1:4) |
| N-2-hydroxyethyl acrylamide/dodecyl acrylate | (1:8) |
| N-2-hudroxyethyl acrylamide/octyl methacrylate | (1:10) |
| N-hydroxymethyl acrylamide/stearyl acrylate | (1:3) |
| N-2-hydroxyethyl methacrylamide/octyl acrylate /myristyl acrylate | (1:8) (1:6) |
| bis-(N-2-hydroxyethyl)acrylamide/octyl methacrylate | (1:12) |
| bis-(N-2-hydroxyethyl)acrylamide/dodecyl acrylate | (1:8) |
| bis-(N-2-hydroxyethyl)methacrylamide/decyl acrylate | (1:10) |
| bis-(N-2-hydroxyethyl)methacrylamide/decyl acrylate | (1:4) |

EXAMPLE 4

Cosmetic emulsions based on Vaseline ®/decyl oleate mixture

A mixture of 7 gm of N-hydroxymethyl acrylamide/dodecyl acrylate copolymer (1:6 molar ratio), 10 gm Vaseline ®, 15 gm of decyl oleate, 3 gm of beeswax, and 2 gm of calcium stearate was melted together by heating to 65° C. Into this mixture were stirred 63 gm of water, heated to 65° C., and the stirring was continued until the emulsion became cold. A cream was obtained which resembled the other two creams described above in its stability properties. By incorporating conventional cosmetically effective substances and perfume oils, a large number of cosmetic creams can be produced based on this basic cream.

The N-hydroxymethyl acrylamide/dodecyl acrylate copolymer (1:6 molar ratio), used as an emulsifier, can be replaced with equally good results by the same amount of N-2-hydroxyethyl acrylamide/octyl methacrylate copolymer (1:10 molar ratio), bis-(N-2-hydroxyethyl)acrylamide/octyl acrylate copolymer (1:12 molar ratio) and the other copolymers mentioned above.

EXAMPLE 5

Cosmetic emulsion based on hardened peanut oil

A mixture of 6 gm of N-hydroxymethyl acrylamide/dodecyl acrylate copolymer (1:6 molar ratio) and 44 gm of hardened peanut oil was melted together by heating to 65° C. Into this mixture were stirred 50 gm of water, which had been heated to 65° C. After stirring until the emulsion was cold, a cream was obtained which resembled to a great extent the previously mentioned creams in its stability properties. The cream can be used as a basic cream for various cosmetic preparations, such as described above.

Replacement of this example of the N-hydroxymethyl acrylamide/dodecyl acrylate copolymer (1:6 molar ratio) by the other copolymers mentioned is readily possible.

We claim:

1. A cosmetic emulsion of the water-in-oil type, comprising (1) from 2% to 20% by weight of statistical copolymers which are composed, in the molar ratio of (I) to (II) of 2:1 to 20:1, of units of the general formulae

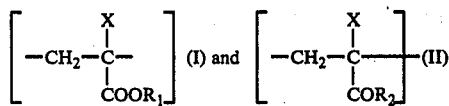

wherein X is hydrogen or a methyl radical, $R_1$ is an alkyl radical of 6 to 24 carbon atoms, and $R_2$ is a radical selected from the group consisting of —NH—$CH_2OH$, —NH—$CH_2CH_2OH$, and —N($CH_2CH_2OH$)$_2$, (2) from 20% to 75% by weight of water, and (3) the remainder to 100% by weight of conventional oily substances used in cosmetic emulsions.

2. The cosmetic emulsion of claim 1 wherein $R_1$ is an alkyl radical of 8 to 14 carbon atoms.

3. The cosmetic emulsion of claim 1 wherein the polymeric emulsifier has an average molecular weight of from 2,000 to 100,000.

4. The cosmetic emulsion of claim 3 wherein the average molecular weight is from 3,000 to 20,000.

5. The cosmetic emulsion of claim 1 wherein the polymeric emulsifier is present in an amount from 5% to 10% by weight, relative to the total cosmetic emulsion.

6. The cosmetic emulsion of claim 5 wherein the water is present in an amount of from 45% to 65% by weight, relative to the total cosmetic emulsion.

7. The cosmetic emulsion of claim 1 wherein, in addition to the polymeric emulsifier and water, there are present vegetable or animal fats, waxes, fatty alcohols and hydrocarbons as said oily substances.

8. In the method of producing a cosmetic emulsion of the water-in-oil type comprising mixing an emulsifier capable of forming water-in-oil creams with a cosmetically acceptable oily material at elevated temperatures, mixing therewith from 20% to 75% by weight of water, cooling under agitation and recovering said cosmetic emulsion of the water-in-oil type, the improvement consisting of adding (1) from 2% to 20% by weight of the statistical copolymer of claim 1, (2) from 20% to 75% by weight of water and (3) the remainder to 100% by weight of conventional oily substances used in cosmetic emulsions.

9. A composition which when agitated with water forms a cosmetic emulsion of the water-in-oil type, comprising (1) from 2% to 20% by weight of the statistical copolymer of claim 1, and (2) the remainder to 100% by weight of the composition of conventional oily substances used in cosmetic emulsions.

10. The cosmetic emulsion of claim 1 wherein the molar ratio of (I) to (II) is 3:1 to 12:1.

* * * * *